United States Patent [19]

Lübbers et al.

[11] 4,230,122
[45] Oct. 28, 1980

[54] TRANSCUTANEOUS MONITORING OF CRITICAL PERFUSION-EFFICIENCY SITUATIONS

[75] Inventors: Dietrich W. Lübbers, Dortmund; Albert Huch, Marburg, both of Fed. Rep. of Germany

[73] Assignee: Max Planck Gesellschaft fuer Foerderung der Wissenschaften, Goettingen, Fed. Rep. of Germany

[21] Appl. No.: 937,946

[22] Filed: Sep. 14, 1978

[30] Foreign Application Priority Data

Aug. 22, 1977 [DE] Fed. Rep. of Germany ....... 2737709

[51] Int. Cl.³ .......................... A61B 5/00; A61B 5/02
[52] U.S. Cl. ..................................... 128/635; 128/691
[58] Field of Search ............... 128/632, 654, 635, 668, 128/691, 670, 736

[56] References Cited

U.S. PATENT DOCUMENTS

| | | | |
|---|---|---|---|
| 3,504,664 | 4/1970 | Haddad | 128/635 |
| 3,623,473 | 11/1971 | Andersen et al. | 128/691 |
| 3,659,586 | 5/1972 | Johns et al. | 128/635 |
| 3,795,239 | 3/1974 | Eberhard et al. | 128/635 |
| 3,918,434 | 11/1975 | Lubbers et al. | 128/654 |

FOREIGN PATENT DOCUMENTS

2514478 10/1975 Fed. Rep. of Germany ........... 128/632
1394171 5/1975 United Kingdom ..................... 128/635

*Primary Examiner*—Robert W. Michell
*Assistant Examiner*—Arthur S. Rose
*Attorney, Agent, or Firm*—Michael J. Striker

[57] ABSTRACT

First and second probes are laid against the skin to transcutaneously measure perfusion and e.g., oxygen concentration and generate corresponding first and second signals. These signals are fed to a signal-processing unit which triggers an alarm whenever changes in these signals meet predetermined rate-of-change criteria. Among these criteria is parallel increase in both perfusion and e.g., oxygen concentration, parallel decrease in both perfusion and e.g., oxygen concentration, and unchanging perfusion accompanied by decreasing e.g., oxygen concentration. The probes are occasionally pressed against the skin, for example under the control of a timer, with a pressure in excess of 1 g/cm², to occasionally induce hyperemic conditions and see whether parallel changes in perfusion and concentration result.

34 Claims, 14 Drawing Figures

TRANSCUTANEOUS MONITORING OF CRITICAL PERFUSION-EFFICIENCY SITUATIONS

BACKGROUND OF THE INVENTION

The present invention concerns the transcutaneous determination of perfusion efficiency in tissue through which blood is being perfused. Such a determination can be performed using a concentration-sensing probe which is laid against the skin surface and serves to ascertain the concentration of a substance, such as oxygen, transported by the perfused blood, along with a perfusionsensing probe which likewise is laid against the skin surface and serves to ascertain the perfusion rate. U.S. Pat. No. 3,918,434 discloses a single probe capable of performing both these measurements, in order to be able to ascertain perfusion efficiency; the disclosure of that patent is incorporated herein by reference, for background information concerning perfusion efficiency and its measurement.

With apparatuses capable of measuring perfusion efficiency, it is frequently necessary to be able to ascertain the maximum limit case of perfusion efficiency, i.e., the case wherein the arterial and transcutaneous concentrations of the indicator substance of interest are equal.

For example, if the delivery of the indicator substance to tissue by the capillaries feeding such tissue is so low that no perfusion-independent concentration field of the indicator substance is formed, then likewise transcutaneous measurement of the arterial concentration of the indicator ceases to be possible, because the arterial indicator concentration is not fully communicated to the skin surface.

Such a critical case can be ascertained by observing changes in perfusion accompanied by simultaneous and parallel changes in the transcutaneously measured indicator concentration.

In the minimum limit case, in contrast, the perfusion disappears, whereas in the maximum limit case the indicator concentration is independent of perfusion.

A perfusion efficiency lower than that of the maximum limit case is also of pathophysiological significance.

Apparatuses which generate the measurement data needed to determine perfusion efficiency—i.e., transcutaneously measured indicator concentration and perfusion—are frequently employed in intensive-care installations. Attempts to use such apparatus in intensive-care installations to monitor perfusion efficiency over long periods of time are very inconvenient and impractical.

Even if the apparatus generating the measurement data needed to determine perfusion efficiency is also set-up to determine perfusion efficiency per se—i.e., as in U.S. Pat. No. 3,918,434—, the problem remains that, in long-term intensive-care contexts, direct observation of perfusion efficiency is not sufficient for the needs of the situation. In particular it is parallel changes in the two parameters (indicator concentration and perfusion) which together characterize perfusion efficiency that are important, and which justify the generation of alarm signals signalling a critical situation requiring emergency counter-measures.

SUMMARY OF THE INVENTION

Accordingly, it is the general object of the present invention to provide an apparatus capable of automatically generating an alarm signal, when the signals produced by the probes measuring indicator concentration and perfusion change in ways actually calling for attention or emergency countermeasures.

In accordance with a general concept of the invention, this is achieved by applying the signal generated by the indicator-concentration-measuring probe and the signal generated by the perfusion-measuring probe to an electronic signal-processing unit operative for evaluating signal changes and triggering an alarm when the detected signal changes meet predetermined criteria.

The advantage of such an apparatus is that it greatly simplifies intensive-care monitoring of an individual patient, without the need to continually monitor all the data being generated in the course of ongoing monitoring of perfusion efficiency.

Also, in those situations where perfusion efficiency per se is not of interest and where instead it is for example oxygen concentration per se which is to be ascertained, e.g., for experimental purposes, the apparatus of the present invention can make it possible to determine the presence of the conditions prerequisite to accurate transcutaneous measurement of arterial indicator concentration.

In one preferred embodiment of the invention, the signal-processing unit is provided with an operational-amplifier function generator, which receives the perfusion signal and the concentration signal and form a signal corresponding to for example, the product thereof. To ascertain the rate of change of the resultant signal, this signal is then applied to two clocked storage units, the outputs of which are connected to respective inputs of a subtractor. The two storage units are clocked alternately, e.g, by clock-pulse trains which are 180° phase-shifted. As a result, at any given time, the difference in the values stored by the two storage units indicates the rate of change of the combined signal, i.e., the change occuring during the time intermediate two clocking pulses. The output signal of the subtractor is applied to the input of a threshold circuit, and the output signal of the latter is applied to an alarm.

In the quite simple embodiment just mentioned, the result achieved makes for only a coarse automatic monitoring of perfusion efficiency data. In particular, in such embodiment an alarm is automatically triggered even in the case where only one of the two parameters in question exhibits a marked change—a case which usually does not represent a critical situation. Monitoring personnel in such instances must, in response to such alarm, ascertain that a critical situation has not actually occurred.

Accordingly, to increase the significance of a generated alarm signal, another embodiment of the invention comprises a two-channel signal-processing unit, one channel processing the perfusion signal and the other the concentration signal. Each channel evaluates changes in the respective signal, preferably by forming the time-differential quotient or else the time derivative of the signal and by then ascertaining the sign (positive or negative) of the change. The thusly generated data concerning the sign of the change in the two signals are then combined by interconnected logic gates, to produce an output signal which triggers an alarm, if the combination of signal changes warrants an alarm. For example, the logic gates may comprise mainly a first AND-gate receiving signals at both its inputs when both the signals in question are increasing in value, a second AND-gate receiving signals at both its inputs when both signals in question are decreasing in value, and an OR-gate having inputs connected to the AND-gate outputs and having an output connected to the alarm.

In this way, only when the concentration signal and the perfusion signal are both changing, and changing in parallel, is an alarm generated.

In a preferred embodiment, the two channels in question, i.e., one for the perfusion signal the other for the concentration signal, each comprise an adjustable-gain amplifier receiving the respective signal; connected to the output thereof a clocked integrator clocked by an adjustable-frequency clock-pulse generator; connected to the output of the clocked integrator a threshold stage; connected to the output of the latter a clocked analog-to-digital converter; connected to the output of the latter two clocked storage units, the clock-pulse generator for the latter furnishing pulses at an adjustable frequency to the clocked converter, and clocking the two storage units in 180° phase-shifted alternation at one-half the adjustable frequency; and a subtractor receiving the output signals of the two storage units and producing, on different output lines, signals indicating the sign of the formed difference. The positive-change output lines of the subtractors of the two channels are both connected to a first AND-gate, and the negative-change output lines to a second AND-gate, the outputs of the two AND-gates being connected via an OR-gate to the alarm.

This preferred embodiment is particularly advantageous with respect to optimizing the signal-to-noise ratio of the signals being processed, especially by being able to adjust the frequency of the clock-pulse generator responsible for clocking the integrators.

The embodiment in question can be further improved, by providing monostable multivibrators in each of the aforementioned subtractor output lines. In that event, if the concentration and perfusion signals are changing more or less in parallel, but not perfectly simultaneously, the signals produced by the monostable multivibrators convert the subtractor output signals into signals better suited for application to the aforementioned AND-gates.

According to a further concept of the invention, the subtractor in the perfusion-signal channel is furthermore provided with a zero output, at which a signal is produced when there is neither a positive nor a negative change in the perfusion signal. This output line, and also the negative-change output line of the subtractor in the concentration-signal channel, are connected to inputs of a third AND-gate, whose output is connected to a further input of the aforementioned OR-gate. Accordingly, an alarm will also be triggered when the perfusion rate stays constant but nevertheless the transcutaneously measured indicator concentration begins to drop. This is of significance, for example, when oxygen delivery is not being maintained despite full perfusion, e.g., because of blockages in small capillary blood circuits.

It is furthermore advantageous to provide an integrator intermediate the output of the OR-gate and the alarm generator. This prevents the premature triggering of alarms, when the apparatus is in the course of being set up, e.g., when the measuring probes are being put into position against the skin surface.

As already explained, direct automatic monitoring of perfusion efficiency per se may not lead to the best or most physically significant alarm system, because critical perfusion-efficiency situations are consituted not merely by changes in perfusion efficiency, but more so by parallel changes in the two parameters (indicator concentration and perfusion) determinative of perfusion efficiency. Accordingly, to be able to automatically detect critical perfusion-efficiency situations, it may be desired to automatically induce perfusion changes, in order to automatically monitor whether or not these are accompanied by parallel indicator-concentration changes.

To this end, the present invention contemplates inducing such perfusion changes by pressing the perfusion-sensing probe against the tissue of interest with a pressure of at least 1 g/cm$^2$.

This pressure can be generated using a thermally insulated weight, or by compression springs, or by other pressure-generating means. In this way, the capillaries are pressed closed, so as to deliberately decrease or stop local perfusion.

It is particularly preferred to generate such pressure using either a hydraulic or pneumatic pressure generator, because this facilitates automatic inducing of perfusion changes in a controlled manner, for example using a pump which generates a cyclical pressing force under the control of a timer. This makes it possible to periodically and automatically induce a perfusion change and ascertain the presence or absence of accompanying parallel concentration changes, and thereby periodically generate more complete and informative data concerning, for example, the oxygen-delivery situation in the tissue concerned.

According to a further concept of the invention, a timer is employed to alternately set the working temperature of the perfusion-sensing probe to body-core temperature and to about 43° C., but with the indicator concentration only being measured during the body-core-temperature time intervals. The hyperemic excess resulting from the higher-temperature time interval serves to induce the maximum limit case of perfusion referred to earlier, and furthermore establishes an undisturbed oxygen partial pressure corresponding to the body-core-temperature value.

In order that the measurement not include dead times during the heating-up periods, use can advantageously be made of duplicate concentration-sensing and perfusion-sensing probes. Each of the two perfusion-sensing probes is alternately switched between body-core temperature and about 43° C., but this is done for the two perfusion-sensing probes in 180° phase-shifted alternation. A switchover unit then transmits to the signal-processing unit the signals from that one of the two sets of probes whose perfusion-sensing probe is presently at body-core temperature.

According to a further concept of the invention, the aforementioned subtractor in the concentration-signal channel is likewise provided with a zero output line, on which a signal appears when the concentration signal is exhibiting neither a positive nor a negative change. This zero signal controls a switch connected to an auxiliary oxygen-concentration-sensing probe. The latter is provided with a skin-contact membrane whose diffusion resistance is high compared to the diffusion resistance of skin (e.g., one or more orders of magnitude higher). Such a probe is capable of producing an extremely accurate or virtually absolute oxygen-concentration signal, i.e., when the oxygen concentration is exhibiting little or no fluctuation, and this probe is operatively connected to an indicator device each time that a signal appears on the zero output line of the subtractor in the concentration-signal channel.

According to another concept of the invention, use is made of more than one concentration-sensing probe, so as to be able to simultaneously measure the concentrations of plural indicators. In that case, the signal-processing unit can comprise further concentration-signal channels, all finally leading to the OR-gate at the input of the alarm generator.

In this way, it is possible to simultaneously monitor e.g. both $O_2$-concentration and $CO_2$-concentration, and thereby more fully monitor the status of intensivecare patients.

When plural concentration-sensing probes are utilized, it is preferable that they cooperate with a common perfusion-sensing probe, all of the probes being constructed as a single unit which can be laid as a whole against the skin surface.

In order to eliminate the temperature-dependence of the indicator concentration, it is contemplated to control the gain of a variable-gain amplifier by means of a temperature sensor in such a manner as to exactly cancel out temperature-dependence. This improves the quality of the evaluations performed by the signal-processing unit.

According to a further concept of the invention, plural concentration-sensing probes are utilized, and their respective signals are combined, for example by means of an operational-amplifier function generator, to develop (in accordance with known, standard relationships) a signal indicating the value of a still further physiological variable, and then it is the latter signal which is applied to the signal-evaluating unit, instead of or in addition to the individual concentration signals.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWING

FIGS. $4b_1$ to $4b_3$ depict the clock pulses applied by unit 4 of FIG. 4 to units 103, 401, 1042, 4020, 1041 and 4021 of FIG. 4.

DESCRIPTION OF THE PREFERRED EMBODIMENTS

Figure 1:
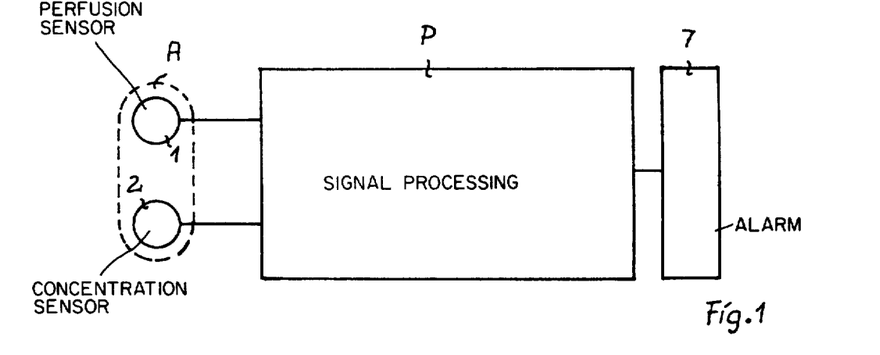
FIG. 1 schematically depicts the simplest version of the invention.

FIG. 1 is a very simplified depiction of the inventive apparatus. Numerals 1 and 2 respectively denote the perfusion-sensing probe and the concentration-sensing probe of the apparatus. Preferably, the two probes are structurally integrated to form a single probe unit A, for example in the manner disclosed in U.S. Pat. No. 3,918,434. Alternatively, the two probes 1, 2 can be laid against the skin or tissue surface separately. The signals generated by the probes 1, 2 are applied to an electronic signal-processing unit P, which produces an output signal when the input signals exhibit marked changes exceeding predetermined rate-of-change criteria for which the signal-processing unit 2 has been adjusted in advance. The output signal of signal-processing unit P then triggers an alarm generator 7. Parallel changes in the two signals indicate an insufficient supply of indicator substance, e.g., oxygen, to the tissue through which blood is being perfused, and the illustrated apparatus will generate an alarm in this critical situation. Also, if only a concentration measurement is to be performed, the alarm signal can be used to indicate that true concentration cannot be accurately measured, due to a too high relative consumption of indicator substance, e.g., oxygen, in the tissue of interest.

Figure 2:
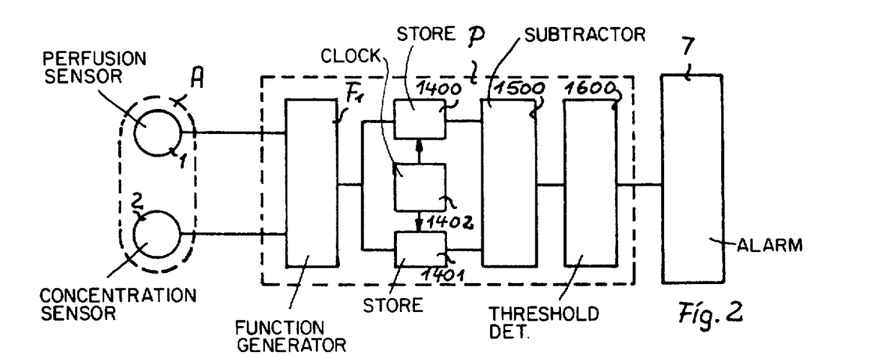
FIG. 2 depicts in greater detail a very simple embodiment.

A very simple version of the signal-processing unit P is schematically depicted in FIG. 2. The two signals from probes 1, 2 are applied to the inputs of an operational-amplifier function generator $F_1$, which combines these signals to form a third function. In general, the third function can be a product of the two probe signals, exponential function thereof or a nomographic function.

The third function need only meet the requirement that the largest possible signal be produced at those times when concentration becomes a function of perfusion. This assures that an easily recognized signal condition, triggering the alarm generator 7, will exist when the two signals from probes 1, 2 are exhibiting small but parallel changes. The output signal of function generator $F_1$ is applied to two clocked storage units 1400, 1401, e.g., sample-and-hold stages. A clock pulse generator 1402 clocks the storage units 1400, 1401 in 180° phase-shifted alternation. The signals held by storage units 1400, 1401 are applied to the two inputs of a subtractor 1500, the output signal of the latter indicating the change in the output signal of $F_1$ over the interval intermediate successive clock pulses, and therefore the rate of change of such signal with respect to time. The output signal of subtractor 1500 is applied to a threshold circuit 1600, which passes signals (whether positive or negative) only if their magnitude exceeds a predetermined value, in order to suppress the effect of insignificantly small signal changes. When threshold circuit 1600 produces an output signal, the alarm generator 7 is triggered.

The FIG. 2 embodiment provides only a relatively coarse monitoring action. It cannot discriminate between a high signal caused by small parallel changes in both probe signals and a high signal caused by larger changes in only one of the two probe signals.

Figure 3:
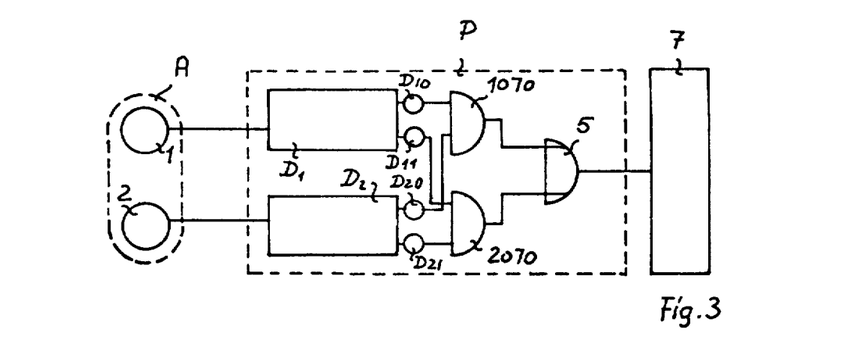
FIG. 3 depicts an embodiment generating higher-significance information.

The embodiment depicted in FIG. 3 can make this discrimination. Here, the signal-processing unit P is two-channel, having one channel processing the perfusion signal from probe 1, and another processing the concentration signal from probe 2. The two channels are provided with respective differential time quotient stages $D_1$, $D_2$. Each of stages $D_1$, $D_2$ can be comprised of exactly the configuration 1400, 1401, 1402, 1500 shown in FIG. 2, the only difference being that the subtractor should be provided with a polarity discriminator, so that the stages $D_1$, $D_2$ can have positive- and negative-polarity outputs $D_{10}$, $D_{11}$ and $D_{20}$, $D_{21}$. It is preferred to use differential time quotient stages (like 1400, 1401, 1402, 1500 in FIG. 2) instead of straight differentiators, because of the greater sensitivity and accuracy for slow signal changes.

The positive polarity outputs $D_{10}$, $D_{20}$ of the two differential time quotient stages $D_1$, $D_2$ are connected to respective inputs of a first AND-gate 1070, and the negative-polarity outputs $D_{11}$, $D_{21}$ to a second AND-gate 2070. The AND-gate outputs are connected via an OR-gate 5 to the alarm generator 7. An alarm is triggered if, and only if, the signals from the two probes 1, 2 are exhibiting parallel changes, i.e., both increasing or both decreasing.

Figure 4:
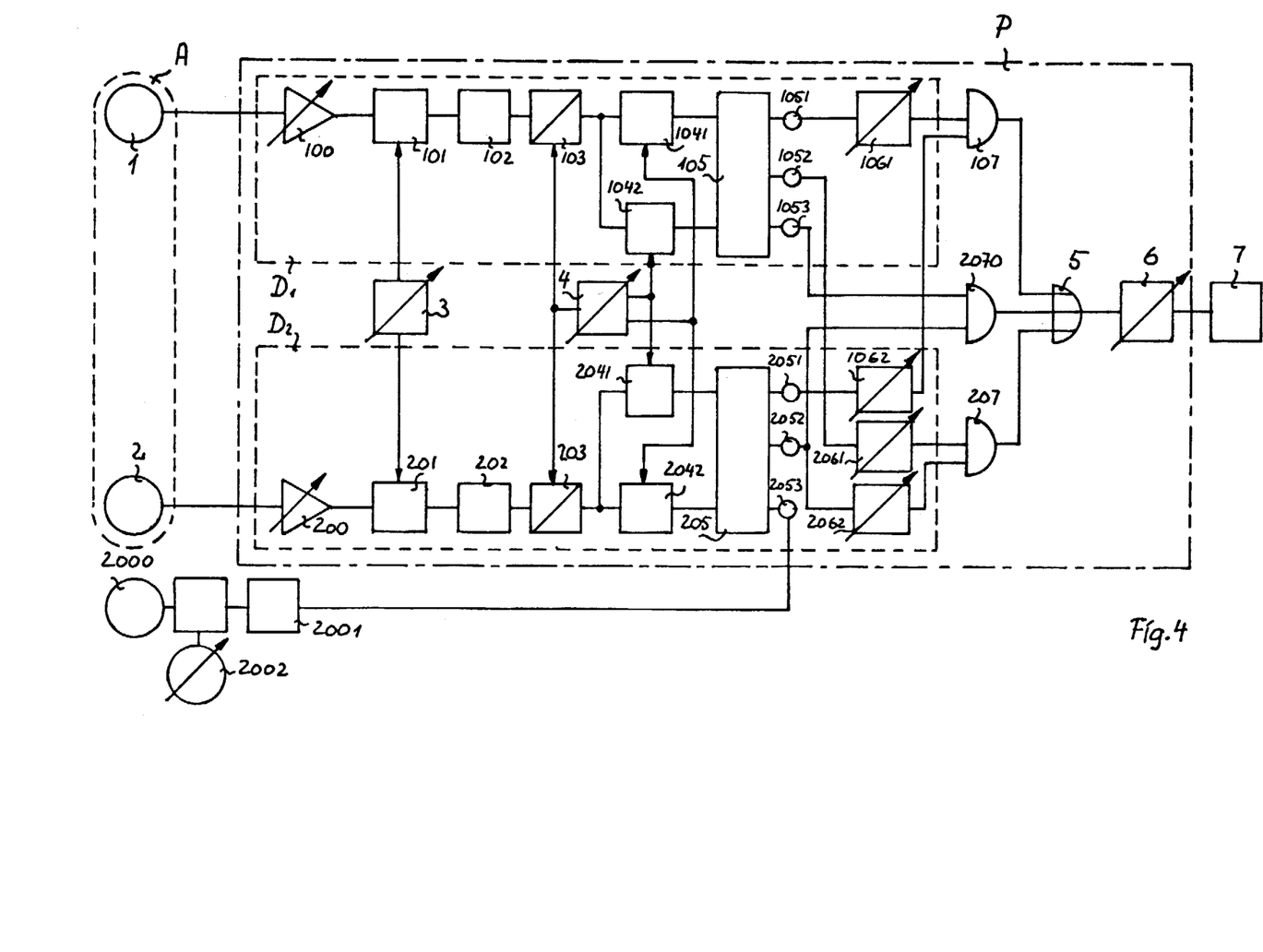
FIG. 4 depicts an embodiment generating still higher-significance information.

FIG. 4 depicts a somewhat more complex embodiment, generating additional information, and also somewhat more accurate and reliable from a signal-processing viewpoint. For explanatory purposes, it is assumed that the indicator substance is oxygen. Again, the signals from the perfusion-sensing probe 1 and the concentration-sensing probe 2 are processed in respective signal channels $D_1$ and $D_2$. The two channels $D_1$, $D_2$ are of identical configuration, share two clock-pulse generators 3, 4, and are interconnected at their outputs by logic gates.

Figure 4A:
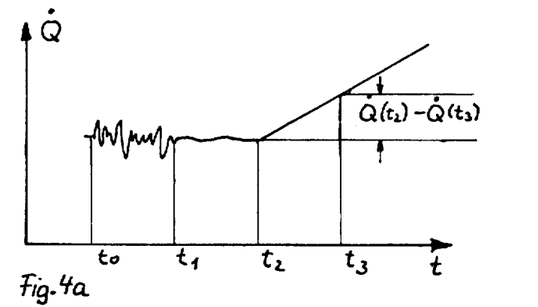
FIG. 4a graphically depicts certain signal-processing operations occurring in the embodiment of FIG. 4.
Figure 4B:
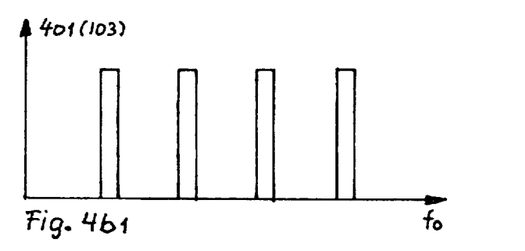
Figure 4B:
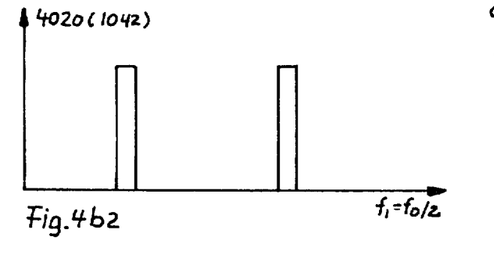
Figure 4B:
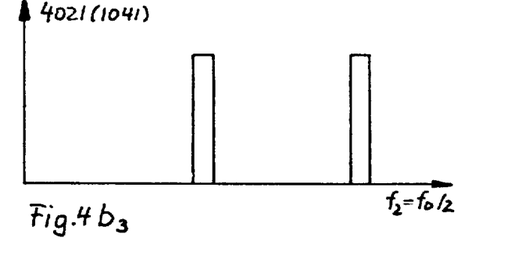

Each of the two channels $D_1$ and $D_2$ operates as follows:

The respective probe signal is transmitted through a preadjusted adjustable-gain amplifier 100 to a clocked integrator 101 clocked by clock-pulse generator 3. The integration interval is so selected as to average out high-frequency noise in the signal, while transmitting slower fluctuations in the signal, i.e., slower than noise. FIG. 4a depicts the signal $\dot{Q}$ a. if no integrator 101 were present, for the time interval $t_0$ to $t_1$;

b. with the integrator 101 present, for the time interval $t_1$ to $t_2$; and c. with the integrator 101 present, for the time interval $t_1$ to $t_2$, the probe signal here changing in value.

A threshold stage 102 connected to the output of integrator 101 passes signals only if their magnitude exceeds a predetermined value, serving in this way merely to suppress signal noise.

The signal $\dot{Q}$, after passing through threshold stage 102, is applied to a clocked analog-to-digital converter 103, and after conversion to digital form is applied to the inputs of two clocked storage units 1041, 1042. The analog-to-digital converter 103 is clocked by clock-pulse generator 4 with a clock-pulse repetition frequency $f_0$ as shown in FIG. $4b_1$. Clock pulse generator 4 also clocks the two storage units 1401, 1042 with clock-pulse repetition frequencies $f_1$ and $f_2$, each equal to $f_0/2$ but 180° phase-shifted relative to each other as shown in FIGS. $4b_2$ and $4b_3$. In this way, the values of, for example, $\dot{Q}(t_2)$ and $\dot{Q}(t_3)$ are stored in respective ones of storage units 1041 and 1042. These two stored values are subtracted by a subtractor 105, i.e., to produce $\dot{Q}(t_3)-\dot{Q}(t_2)$. Only the sign of this difference is of interest in this embodiment. Accordingly, the subtractor 105 is provided with internal polarity-discriminating means, so that signals will appear on its three outputs 1051, 1052, 1053 as follows: a signal on output 1051 when $\dot{Q}(t_3)-\dot{Q}(t_2)>0$; a signal on output 1052 when $\dot{Q}(t_3)-\dot{Q}(t_2)<0$; and a signal on ouput 1053 when $\dot{Q}(t_3)-\dot{Q}(t_2)=0$.

The corresponding components in concentration-signal channel $D_2$ operate in exactly the same way.

The plus outputs 1051, 2051 of the two channels are connected to respective inputs of an AND-gate 107, the minus outputs 1052, 2052 to an AND-gate 207. If the two probe signals are changing in parallel, i.e., both increasing or both decreasing, then AND-gate 107 or AND-gate 207 produces an output signal, respectively. If an output signal is produced, it is transmitted via OR-gate 5 and triggers alarm generator 7.

It may happen that the changes in the two probe signals, although parallel, commence non-simultaneously, i.e., one commencing after a time delay subsequent to the commencement of the other. To take this into account, the subtractor output lines 1051, 1052, 2051, 2052 are provided with respective adjustable time-delay stages 1061, 1062, 2061, 2062, here in the form of adjustable monostable vibrators. These are set to appropriate respective time-delay values, to compensate for the differing time delays in the plural channels.

If, with the perfusion rate constant, the oxygen partial pressure nevertheless commences to decrease, this constitutes a critical situation. To be able to detect this situation, a further AND-gate 2070 has a first input connected to the zero output 1053 of the subtractor 105 of the perfusion-signal channel, and a second input connected to the minus output 2052 of the subtractor 205 of the concentration-signal channel. AND-gate 2070 produces an output signal and thereby triggers alarm generator 7, when the perfusion is constant but the oxygen concentration nevertheless decreasing.

An adjustable integrator 6 is connected intermediate OR-gate 5 and alarm generator 7. Certain tissue types exhibit marked parallel fluctuations in the course of assuming a steady response to changed metabolic conditions. The adjustable integrator 6 is set to charging and discharging time-constant values such as to average-out the OR-gate output signal over a time interval corresponding to several such fluctuations in the particular type of tissue involved. This prevents premature triggering of an alarm.

When oxygen concentration per se is of especial interest, then the FIG. 4 embodiment is advantageously supplemented by an auxiliary oxygen-concentration-sensing probe 2000, which may be of the same design as concentration probe 2 but provided with a skin-contact membrane having a diffusion resistance which is high compared to skin diffusion resistance. Such a concentration probe is capable of measuring oxygen pressure with extreme accuracy, provided that there are no fluctuations in the oxygen pressure. However, the absence of fluctuation in the oxygen pressure is indicated, in the FIG. 4 embodiment, by the appearance of a signal at the zero output 2053 of the subtractor 205 in the concentration-signal channel $D_2$, i.e., in accordance with $$pO_2(t_1)-pO_2(t_2)=0.$$

Accordingly, the signal at zero output 2053 can be used to control a switch 1001 which when activated operatively connects the auxiliary concentration-sensing probe 2000 to an indicator or recorder 2002, for extreme-accuracy oxygen measurements whenever conditions permit.

Figure 5:
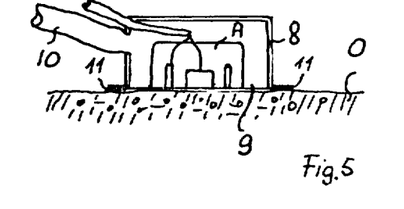
FIG. 5 depicts a device for inducing perfusion changes.

In order to be able to deliberately induce perfusion changes by means of hyperermia, it is necessary to apply to the tissue surface a pressure of at least 1 g/cm$^2$. FIG. 5 is a simple depiction of a device capable of periodically inducing perfusion changesby means of hyperemia. Essentially, the structure shown in FIG. 5 is an ordinary concentration- and/or perfusion-sensing probe, but the interior of the probe housing 8 is connected on via a tube 10 to a (non-illustrated) pump. The pump is periodically activated by a timer device, and periodically boosts the pressure applied by skin-contact membrane 9 to the skin against which the probe is laid. The probe as a whole is held in place against the skin by an elastic sleeve 11, for example surrounding an extremity of a patient's body. By periodically boosting the applied pressure in this way, so as to periodically or intermittently cut off local perfusion by means of hyperemia, the monitoring apparatus is able to ascertain whether the aforementioned maximum limit case of perfusion efficiency is in existence.

Instead of the structure shown in FIG. 5, the probe can be provided at the inward face of an inflatable cuff, the inflation pressure of the cuff being periodically boosted by a timer-controlled pump.

Figure 6:
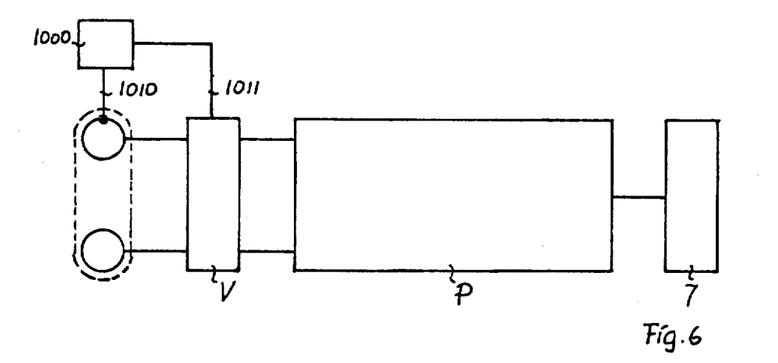
FIG. 6 depicts an embodiment of the invention in which the perfusion-sensing probe is switched back and forth between two temperatures.

FIG. 6 depicts an embodiment of the invention, again making use of a two-channel signal-processing unit P such as already described. However, here, the working temperature of the perfusion-sensing probe 1 is caused to alternately assume a value of about 43° C. and then body-core temperature which is usually about 37° C. The temperature alternation is effected by periodically changing the electrical heating power supplied to the perfusion-sensing probe 1, using a timer-controlled heating-power adjuster 1000. The heating-power adjuster 1000 is controlled by a temperature sensor 1010, which latter senses the working temperature of the probe and feeds a corresponding temperature signal back to adjuster 1000. A control line 1011 is connected to an interlock unit 1011, which permits transmission of the two probe signals to the signal-processing unit P, only when the working temperature of the perfusion-sensing probe 1 is at the body-core-temperature value of ca. 37° C. During the intervals of lower, body-core working temperature, there remains for a while a condition of hyperemic superabundance left over from the 43° C. working-temperature time intervals. As a result, on the one hand, there is established the maximum possible perfusion, but at the same time the oxygen pressure assumes a value corresponding to the arterial value at body-core temperature.

Figure 7:
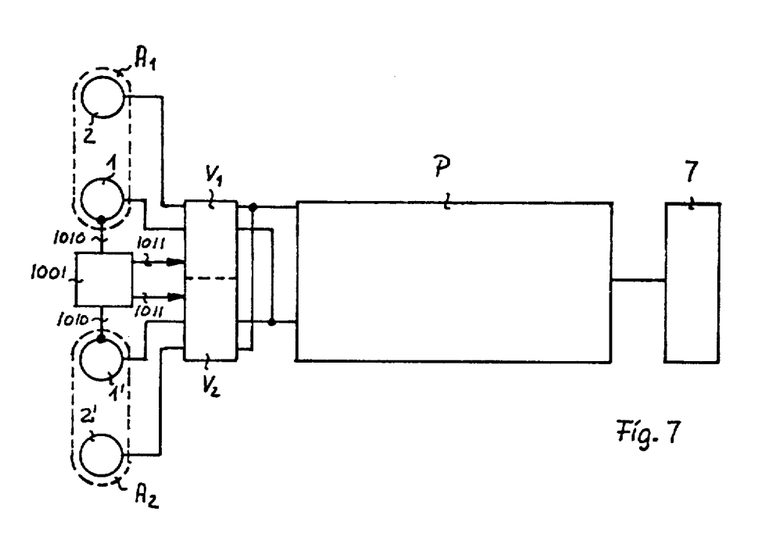
FIG. 7 depicts an embodiment of the invention provided with two sets of alternately used sensing probes.

FIG. 7 depicts an embodiment based on FIG. 6, but unlike FIG. 6 not exhibiting periodic dead times during which measurement cannot be performed. In FIG. 7, use is made of two sets A, A' of probes 1, 2 and 1', 2'. The working temperature of the perfusion-sensing probe 1 or 1' is, as in FIG. 6, alternated between ca. 43° C. and body core temperature of ca. 37° C., under the control of temperature sensors 1010 and a timer 1001. However, the timer 1001 causes the alternation of the working temperature of the two perfusion-sensing probes 1, 1' to be 180° phase-shifted, i.e., so that when probe 1 is at a working temperature of 43° C. probe 1' is at a working temperature of 37° C., and vice versa, so that always one of the two perfusion-sensing probes 1, 1' will be at a body-core temperature of ca. 37° C. The output signals from the probes 1, 2 and 1', 2' are applied to signal-processing unit P alternately, via a changeover unit comprising two switching stages $V_1$, $V_2$ controlled via control lines 1011. When the perfusion-sensing probe 1 is at body-core temperature and probe 1' at 37° C., the signals from probes 1, 2 are applied to unit P; when perfusion-sensing probe 1' is at body-core temperature and probe 1 at 37° C., then it is the signals from probes 1',2' which are transmitted to signal-processing unit P.

Figure 8:
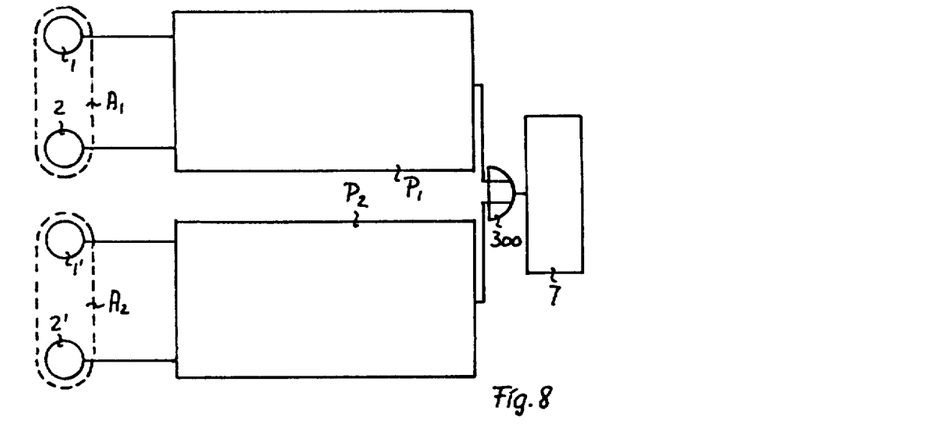
FIG. 8 depicts an embodiment capable of evaluating perfusion efficiency with respect to two different indicators.

FIG. 8 depicts an embodiment provided with two two-channel signal-processing units $P_1$, $P_2$ and two sets $A_1$, $A_2$ of sensing probes 1, 2 and 1', 2', capable of monitoring perfusion efficiency with respect to two different indicator substances simultaneously. For example, a critical physiological situation is in existence, if the concentration of blood $CO_2$ fluctuates in parallel with perfusion. The probe 1 of the probe unit $A_1$ senses $O_2$ concentration, whereas the probe 1' of probe unit $A_2$ senses $CO_2$ concentration. The two signals from each probe unit $A_1$ or $A_2$ are applied to their respective signal-processing units $P_1$, $P_2$ and processed in any of the ways described above. The output lines of the two signal-processing units $P_1$, $P_2$ are connected to the alarm generator 7 via an OR-gate 300. An alarm is triggered whenever perfusion efficiency exhibits critical behavior with respect to either $O_2$ or $CO_2$ concentration. In this connection, it is well known that both $O_2$ and $CO_2$ concentrations are proportional to pressure in accordance with Henry's Law $$\alpha \cdot pO_2 = C$$

wherein $\alpha$ is the solubility coefficient, $pO_2$ the oxygen partial pressure, and C the concentration, so that the concentrations of $O_2$ and $CO_2$ are advantageously determined by measurement of partial pressure.

Figure 9:
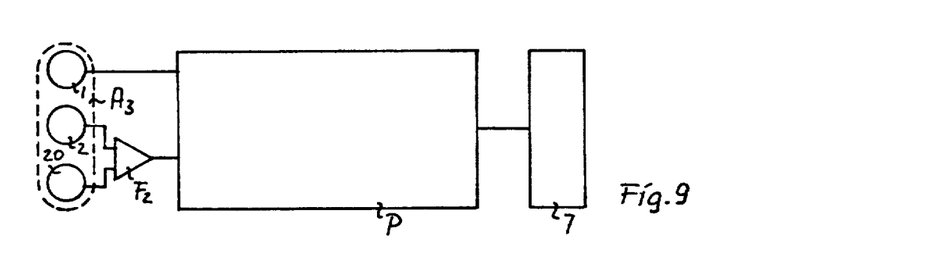
FIG. 9 depicts an embodiment in which perfusion efficiency is evaluated with respect to a variable whose value is derived from the concentrations of plural indicators.

In the embodiment depicted in FIG. 9, the probe unit $A_3$ comprises two concentration-sensing probes 2, 20 for two different indicator substances, both cooperating with a common perfusion-sensing probe 1. The output signals from the two concentration-sensing probes 2, 20 are applied to an operational-amplifier function generator $F_2$ serving to generate a signal dependent upon these first two signals. For example, by means of known nomographic functions a signal indicating pH can be derived from signals indicating $O_2$ concentration and $CO_2$ concentration; or as another example, after ascertaining the solubility coefficient for oxygen, one can derived a signal indicating the hemoglobin saturation of the blood. Then, it is this derived signal which is applied, along with the perfusion signal from probe 1, to the signal-processing unit P and processed in any of the ways described above.

Figure 10:
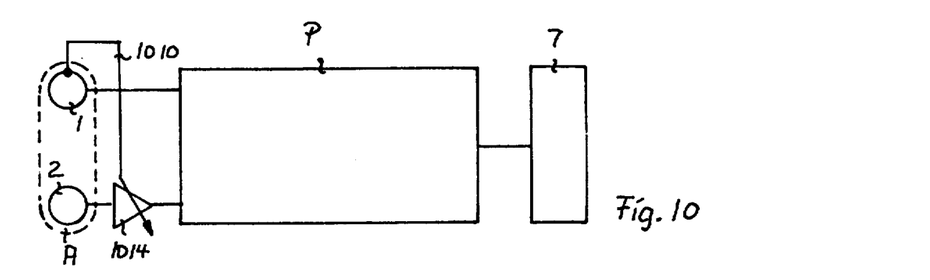
FIG. 10 depicts an embodiment provided with means compensating for the temperature-dependence of indicator concentration.

FIG. 10 depicts an embodiment provided with means compensating for the temperature-dependence of indicator-substance concentration. The output signal from concentration-sensing probe 2 is transmitted to signal-processing unit P via a controllable-gain amplifier 1014, the gain of which is controlled by a temperature sensor 1010 which senses the working temperature of the perfusion-sensing probe 1. The gain of amplifier 1014 is controlled in such a manner as to cancel out or compensate the temperature-dependence exhibited by indicator concentration. The requisite corrective or compensatory values can be obtained once, by using the embodiment depicted in FIG. 6 to ascertain the sensed concentration at 37° C. and at 43° C. and then forming the ratio of those two values. Advantageously, instead of just forming such a ratio, the sensed concentration values at further temperatures in the range between 37° C. and 43° C. are also ascertained, and from all these values a table is formed which can be consulted whenever needed to ascertain the requisite corrective values for temperatures in this range. However, the corrective values for blood can also be calculated, for example, from a bound-$O_2$ curve.

In the embodiments depicted above, it is to be understood that the various features of each can be combined with features of others. For example, the temperature-compensating means in FIG. 10 can be provided for each of the probe units $A_1$, $A_2$ in FIG. 8, and so forth. Likewise, wherever a signal-processing unit P, $P_1$ or $P_2$ is shown as an empty rectangle, it is to be understood that the contents of such rectangle can be as shown in any one of FIGS. 2, 3 and 4. Furthermore, because of the type of signal-processing operations performed, it should be clear that these operations, or their equivalents, can alternatively be implemented by different circuit configurations.

It will be understood that each of the elements described above, or two or more together, may also find a useful application in other types of circuits and structures differing from the types described above.

While the invention has been illustrated and described as embodied in an apparatus automatically triggering an alarm when critical perfusion-efficiency situations are sensed, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus automatically detecting critical perfusion-efficiency situations, comprising, in combination, first means operative for transcutaneously sensing perfusion and generating a corresponding first signal; second means operative for transcutaneously sensing the concentration of an indicator substance transported by the blood perfused through the tissue of interest and generating a corresponding second signal; an alarm generator; and signal-processing means connected to the first and second means for receipt of the first and second signals and connected to the alarm generator and operative for triggering the latter upon detection of signal changes meeting at least one predetermined rate-of-signal-change criterion.

2. The apparatus defined in claim 1, the signal-processing means comprising rate-of-change determining means, the rate-of-change determining means comprising two clocked storage units receiving a signal whose rate of change is to be ascertained, clock-signal generating means clocking the two storage units alternately, and subtracting means subtracting the signals stored by the two storage units.

3. The apparatus defined in claim 1, the signal-processing means comprising means deriving a third signal from the first and second signals and triggering the alarm generator upon detection of changes in the third signal meeting at least one predetermined rate-of-signal-change criterion.

4. The apparatus defined in claim 1, the signal-processing means comprising a function generator receiving the first and second signals and multiplying them to form a third signal, two clocked storage units both receiving the third signal, clock-signal generating means clocking the two storage units periodically with 180° phase-shifted alternation, a subtractor subtracting the signals stored by the two storage units to form a difference signal, and a threshold stage receiving the difference signal and triggering the alarm when the difference signal falls into a predetermined range.

5. The apparatus defined in claim 1, the signal-processing means comprising first and second rate-of-change determining means respectively determining the rate of change of the first and second signals and generating corresponding respective first and second rate-of-change data, and logic circuit means receiving the first and second rate-of-change data and triggering the alarm generator when the first and second rate-of-change data in combination meet at least one predetermined criterion.

6. The apparatus defined in claim 5, the rate-of-change data having the form of increase-signals and decrease-signals indicating whether the first and second signals are increasing or decreasing, the logic circuit means triggering the alarm generator when the first and second signals are both changing in the same direction.

7. The apparatus defined in claim 6, the apparatus furthermore including means automatically operative for periodically pressing at least said first means against the surface of tissue across which the transcutaneous measurements are being performed with a pressure of at least 1 g/cm², whereby to periodically induce perfusion changes in order to ascertain whether the first and second signals will both change in the same direction.

8. The apparatus defined in claim 6, the rate-of-change data furthermore including a zero-change signal indicating that the second signal is not changing, the apparatus furthermore including an auxiliary oxygen-concentration-sensing probe operative for transcutaneously measuring oxygen concentration, the probe being of the type comprising a skin-contact membrane which is laid against the surface of skin across which the transcutaneous measurement is to be made, the skin-contact membrane having a diffusion resistance which is high compared to that of skin, indicating means, and means connected to the probe and indicating means and connected to receive the zero-change signal and in response to the latter transmitting the output signal of the auxiliary probe to the indicating means.

9. The apparatus defined in claim 5, the first rate-of-change determining means having an increase-signal output line and a decrease-signal output line upon which signals appear depending upon whether the first signal is increasing or decreasing, the second rate-of-change determining means having an increase-signal output line and a decrease-signal output line upon which signals appear depending upon whether the second signal is increasing or decreasing, the logic circuit means comprising a first AND-gate having inputs connected to the increase-signal output lines, a second AND-gate having inputs connected to the decrease-signal output lines, an OR-gate having inputs connected to the outputs of the AND-gates and having an output connected to the alarm generator.

10. The apparatus defined in claim 9, the first rate-of-change determining means additionally having a zero output line upon which a signal appears when the first signal is neither increasing nor decreasing, the logic circuit means furthermore including a third AND-gate having inputs connected to the zero output line of the first rate-of-change determining means and to the decrease-signal output line of the second rate-of-change determining means, the OR-gate having a further input connected to the output of the third AND-gate.

11. The apparatus defined in claim 9, the signal-processing means furthermore including an integrator connected between the output of the OR-gate and the alarm generator.

12. The apparatus defined in claim 5, the logic circuit means comprising means triggering the alarm generator when the first and second rate-of-change data in combination indicate that perfusion is not changing but indicator concentration is nevertheless changing.

13. The apparatus defined in claim 5, the first means comprising a perfusion-sensing probe and means heating the probe to maintain the probe at working temperature, the apparatus furthermore comprising means for causing the probe to alternate between a working temperature equal to about 43° C. and a working temperature corresponding to body-core temperature.

14. The apparatus defined in claim 1, the signal-processing means comprising a first and a second signal-processing channel each processing a respective one of the first and second signals, each signal-processing channel comprising an amplifier receiving the respective signal, a clock integrator having an input connected to the output of the amplifier, a threshold circuit stage having an input connected to the output of the integrator, a clocked analog-to-digital converter having an input connected to the output of the threshold circuit stage, two clocked storage units each having an input connected to the output of the converter, a comparator having inputs connected to the outputs of the storage units, the comparator having a positive output on which a signal appears when the difference between the two signals stored by the storage units is positive and also having a negative output on which a signal appears when that difference is negative, the signal-processing means furthermore including shared components shared by the two signal-processing stages, the shared components including first clock-pulse generating means clocking the clocked intergrators in the two signal-processing channels, and second clock-pulse generating means clocking the clocked analog-to-digital converters and the clocked storage units in the two signal-processing channels, the second clock-pulse generating means applying to the converters in both channels clock pulses having a first repetition frequency and applying to the storage units clock pulses having one half the first repetition frequency, the two storage units in the first channel being alternately clocked by 180° phase-shifted clock pulses, the two storage units in the second channel likewise being alternately clocked by 180° phase-shifted clock pulses, the signal-processing means furthermore including a first AND-gate having inputs connected to the positive outputs of the comparators in the two channels, a second AND-gate having inputs connected to the negative outputs of the comparators in the two channels, and an OR-gate having inputs connected to the AND-gate outputs and having an output connected to the alarm generator.

15. The apparatus defined in claim 14, the signal-processing means furthermore including a plurality of adjustable of monostable vibrators, each connected between a respective comparator output and a respective AND-gate input and serving as adjustable compensatory time-delay stages.

16. The apparatus defined in claim 1, the apparatus furthermore including means operative for pressing at least said first means against the surface of tissue across which the transcutaneous measurements are being performed with a pressure of at least 1 g/cm$^2$.

17. The apparatus defined in claim 16, the pressing means including a thermally insulated weight.

18. The apparatus defined in claim 16, the pressing means comprising a hydraulic or pneumatic pressure generator.

19. The apparatus defined in claim 1, the apparatus furthermore including means automatically operative for periodically pressing at least said first means against the surface of tissue across which the transcutaneous measurements are being performed with a pressure of at least 1 g/cm$^2$, whereby to periodically cause perfusion changes.

20. The apparatus defined in claim 1, the first means comprising a perfusion-sensing probe and means heating the probe to maintain the probe at working temperature, the apparatus furthermore comprising means for causing the probe to alternate between a working temperature equal to about 43° C. and a working temperature corresponding to body-core temperature.

21. The apparatus defined in claim 1, the first means comprising a first perfusion-sensing probe and a second perfusion-sensing probe, the second means comprising a first concentration-sensing probe and a second concentration-sensing probe, the apparatus furthermore comprising means causing the working temperature of the first and second perfusion-sensing probes to alternate in such a manner that one is at ca. 43° C. while the other is at body-core temperature, and vice versa, and means operative for applying to the signal-processing means the output signals of the first perfusion-sensing probe and the first concentration-sensing probe when it is the first perfusion-sensing probe which is at a body-core temperature, and for applying the output signals of the second perfusion-sensing probe and the second concentration-sensing probe when it is the second perfusion-sensing probe which is at body-core temperature.

22. The apparatus defined in claim 1, furthermore including a condition-safe indicator, the signal-processing means including means maintaining the condition-safe indicator activated so long as the at least one predetermined rate-of-change criterion is not met.

23. The apparatus defined in claim 1, the second means comprising an $O_2$-concentration-sensing probe provided with an $O_2$-responsive electrode system.

24. The apparatus defined in claim 1, the second means comprising a $CO_2$-concentration-sensing probe provided with a $CO_2$-responsive electrode system.

25. The apparatus defined in claim 1, the second means comprising a plurality of concentration-sensing probes each ascertaining the concentration of a different respective indicator substance.

26. The apparatus defined in claim 25, each concentration-sensing probe producing a respective second signal, the signal-processing means comprising a plurality of signal-processing units each receiving a respective second signal and also a first signal from said first means and producing an output signal when the respective second and first signal exhibit changes meeting at least one predetermined criterion, and an OR-gate connected to receive the output signals of the plural signal-processing units and having an output connected to the alarm generator.

27. The apparatus defined in claim 25, the plural concentration-sensing probes being arranged to form a single structural unit which can be laid as one item against the surface of skin.

28. The apparatus defined in claim 1, the signal-processing means furthermore including a temperature sensor sensing the working temperature of the first means and in automatic dependence thereon altering the second signal to compensate for the temperature dependence of indicator concentration.

29. The apparatus defined in claim 1, the second means comprising a plurality of concentration-sensing probes each operative for transcutaneously sensing the concentration of a different respective indicator, and a function generator receiving the signals produced by the plural concentration-sensing probes and deriving said second signal therefrom.

30. The apparatus defined in claim 29, the plural concentration-sensing probes being an $O_2$-concentration-sensing probe and a $CO_2$-concentration-sensing probe.

31. A method of monitoring critical perfusion-efficiency situations, comprising the steps of transcutaneously sensing perfusion and generating a corresponding first signal; transcutaneously sensing the concentration of an indicator substance transported by the blood perfused through the tissue of interest and generating a corresponding second signal; and feeding the first and second signals to a signal-processing means operative for triggering an alarm upon detection of signal changes meeting at least one predetermined rate-of-change criterion.

32. The method defined in claim 31, the first signal being generated using a perfusion-sensitive probe, furthermore including the step of pressing the probe against the tissue of interest with a pressure equal to at least 1 $g/cm^2$, whereby to deliberately induce a perfusion change.

33. The method defined in claim 32, generating said pressure using a thermally insulated weight.

34. The method defined in claim 32, periodically applying and removing said pressure.

* * * * *